United States Patent [19]
Hostettmann et al.

[11] Patent Number: 5,929,124
[45] Date of Patent: Jul. 27, 1999

[54] ANTIMICROBIAL DITERPENES

[76] Inventors: Kurt Hostettmann, Centre 48, St. Sulpice, Switzerland, 1025; Frederic Schaller, Grand Fontaine 4, 1700 Fribourg, Switzerland

[21] Appl. No.: 08/917,648

[22] Filed: Aug. 22, 1997

[51] Int. Cl.$^6$ .............................. A01N 35/04; C07C 45/00
[52] U.S. Cl. .......................... 514/691; 514/729; 568/338; 568/368; 568/817; 568/822
[58] Field of Search ...................................... 568/373, 338, 568/361, 368, 377, 817, 823, 825, 832; 514/680, 718, 691, 729

[56] References Cited
PUBLICATIONS

"Development and application of a method for screening for antifungal activity (*Candida albicans*) in vegetable extracts," Doctoral Thesis of Lila Rahalison, pp. 142–154, indexed by the Université de Lausanne library Dec. 14, 1994. Two cover pages and pp. 142–154 provided (French). English translation of cover p. 2 and Section 3.3.3 from p. 148 of the thesis provided. 8 pages total, (1994).

*Primary Examiner*—Gary Geist
*Assistant Examiner*—Sreeni Padmanabhan
*Attorney, Agent, or Firm*—Clark & Elbing LLP

[57] ABSTRACT

Antimicrobial diterpenes and methods of using them.

18 Claims, No Drawings

ANTIMICROBIAL DITERPENES

BACKGROUND OF THE INVENTION

The invention features diterpenoids having pharmaceutical activity. *Swartzia madagascariensis* Desv. (Leguminosae) is a tree found throughout tropical Africa. Traditional medicine describes the use of preparations including the root of the tree to treat leprosy and syphilis, and to kill termites. Saponins extracted from the fruit pods are molluscicidal, and can kill snails carrying vectors for schistosomiasis.

SUMMARY OF THE INVENTION

The invention features diterpene derivatives having antimicrobial activity, and methods of using the disclosed compounds for the treatment or inhibition of microbial infections.

The invention provides a compound having the formula (I):

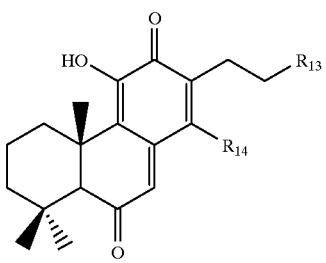

(I)

wherein $R_{14}$ is methyl and $R_{13}$ is hydroxyl; or $R_{13}$ is —O— bonded to $R_{14}$ and $R_{14}$ is —CHOR$_a$—, $R_a$ being hydrogen, $C_{1-4}$ alkyl, or formula (a) below.

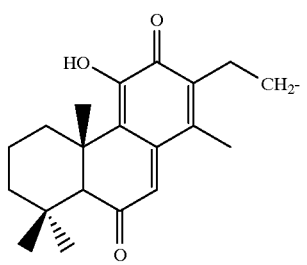

(a)

The compounds of formula (I) can be used, alone or in combination with one or more additional antimicrobial agents, to treat microbial infections such as fungal infections and bacterial infections, or combinations of such infections. The invention includes a method of inhibiting a microbial infection of the skin, hair, or nails. Examples include an infection of a dermatophyte selected from Trichophyton and Epidermophyton spp., and preferably from *T. rubrrum, T. mentagrophytes*, and *E. floccosum*. Other dermatophytes include *Microsporum gypseum, M. nanum, T. verrucosum, C. albicans*, and *Scopulariopsis brevicaulis*. Infections include tinea pedis and particularly onocomycosis. Other aspects of the invention will be apparent from the detailed description, examples, and the appended claims.

DETAILED DESCRIPTION OF THE INVENTION

The invention features antimicrobial diterpenes isolated from the root bark of *S. mgascariensis*. These quinone methide diterpenes have a cassane skeleton, such as (4bR*, 8aR*)-4b,5,6,7,8,8a-hexahydro-4-hydroxy-4b,8,8,1-tetramethyl-2-(2-hydroxy-ethyl) -3,9-phenanthrenedione (formula (i)). These diterpenes may be synthesized according to methods known in the art or obtained as a natural product.

Formulae (i) was isolated as described in Example 1. Plant material was collected in Zimbabwe. A voucher specimen is deposited at the Institute of Pharmacognosy and Phytochemistry, University of Lausanne, Lausanne, Switzerland. Antimicrobial assays are performed by a modification of the broth microdilution susceptibility assay using the tetrazolium salt XTT (Examples 2–6, see summary of results in Table 1 below).

TABLE 1

Activity Summary of Formula (i)

| Assay | IC$_{50}$ (µg/mL) | MIC (µg/mL) |
|---|---|---|
| A. fumigatus | 6.49 | 6.25 |
| C. krusei | 0.55 | 1.56 |
| T. glabrata | 0.44 | 1.65 |
| C. albicans | 0.12 | 0.78 |
| S. aureus | — | 1.56 |
| Vero cell proliferation | 12.7 | — |

Formula (ii) compounds are those compounds of formula (I) wherein $R_{13}$ is —O—bonded to $R_{14}$ and $R_{14}$ is —CHOR$_a$—, $R_a$ being hydrogen, $C_{1-4}$ alkyl, or formula (a). Formula (ii) compounds may be obtained according to Example 7. Activity data for formula (ii) compounds showed antiviral (e.g., anti-HSV-2) and antifungal (e.g., anti-Candida albicans) activity, and cytotoxicity at about 10 times the IC$_{50}$ for antiviral activity. In general, inhibition of a microbial infection means inhibiting microbial growth, relative to an untreated control, by at least 30%, and preferably by 50% or 75%. Cytotoxicity assays utilized the same dye as a marker of cell viability.

The invention also provides prodrugs or metabolic precursors of the disclosed compounds. Examples include pharmaceutically acceptable salts or protected forms of the disclosed compounds (e.g., replacing the hydrogen of a hydroxy group with a hydroxyl protecting group). Examples of protecting groups include carbonate and carbamoyl derivatives.

The following examples are illustrative, and do not limit the scope of the invention.

EXAMPLE 1

Extraction and separation of swartziadione (formula (i))

Dried powdered root bark (500 g) of *Swarizia madagascariensis* was extracted by $CH_2Cl_2$ at room temperature 3×3,000 ml (24 h, 140 rpm shaking). The solvent was removed under reduced pressure (700 mbar, 30° C.) and the $CH_2Cl_2$ extract (47.0 g) was fractionated by column chromatography on silica gel with petroleum ether/EtOAc 2:1 to afford fraction G (3.89 g). This material was purified by medium pressure liquid chromatography on a Diol support with petroleum ether/EtOAc 5:1 to provide crude swartziadione (1.31 g). Crystals were grown from isopropanol as orange needles (0.80 g).

EXAMPLE 2

Inhibition of Candida spp. culture

*Candida albicans* (strain ATCC #90028), *Candida krusei* (strain ATCC #90030), and *Torulopsis (Candida) glabrata* (strain ATCC #6258) were subcultured from cryopreserved stocks onto sabourand dextrose agar plates. Blastoconidia were suspended into RPMI-MOPS (media) and inoculated (500 CFW/well) into 96-well plates containing test compounds in a final volume of 100 µL/well. After 22 hours at 35° C., 25 µL of XTT (2,3-bis(2-methoxy-4-nitro-5-sulfophenyl)-5-[(phenylamino)carbonyl]-2H-tetrazolium hydroxide), (100 µg/mL) with PMS (phenazine methyl sulfate, 5 µM) were added to each well, followed by 2 hours of shaking. Growth was assessed spectrophotometrically by measuring the appearance of soluble formazan stain at 450 nm using an $E_{max}$ microplate reader. Validity of the assay was confirmed by determination of the C. albicans minimum inhibitory concentration (MIC) for known antifungal agents such as amphotericin B, 5-flucytosine, fluconazole, nikkomycin Z, and polyoxin D,which were found to be within reported ranges.

EXAMPLE 3
Inhibition of Staphylococcus aureus culture

Strains of Staphylococcus aureus were subcultured from cryopreserved stocks onto sheep blood agar plates (methicillin-sensitive reference strain ATCC #29213. Methicillin-resistant (MRSA) clinical isolate was obtained from Dr. Gary Doern, Director of Clinical Microbiology, University of Massachusetts Medical Center, Worcester, Mass.). Bacteria were suspended in Mueller Hinton broth and inoculated (5×104 CFU/well) into 96-well plates containing test compounds in a final volume of 100 µL/well. After 24 hours at 35° C., plates were shaken for 1 minute and turbidity was read manually at 650 nm using a $E_{max}$ microplate reader (Molecular Devices, Sunnyvale, Calif. The MIC values of vancomycin and gentamicin in this screening assay are determined to be approximately 1 µg/mL and 0.6 µg/mL, respectively, well within the reported ranges (National Committee on Clinical Laboratory Standards Vol. 14, No. 16, 1994, Table 3).

EXAMPLE 4
Inhibition of Aspergillus spp. culture

Aspergillus fumigatus (strain ATCC#8001) was subcultured from a refrigerated potato dextrose agar slant (immersed in mineral oil) onto a fresh potato dextrose agar slant. After 72 hours of incubation at 37° C., the slants were filled with 7 mL sterile, cold, distilled water and put on ice for 2 hours. After disrupting the tissue, spores were filtered through sterile gauze using a 30 cc syringe. The resulting mixture was centrifuged for 10 minutes at 2,000 rpm. The supernatant was discarded and the pellet was resuspended in 5 mL sterile, distilled water. Spores were diluted in RPMI-MOPS (media) and 98 µL of inoculum (500 CFU/mL) were added to 96 well plates containing 2 µL of each test compound to reach a final volume of 100 µL/well. After 48 hours at 37° C., 21 µL of MEN (menadione 10 mM stock) was added to 12 mL XTT (2,3-bis(2-methoxy-4-nitro-5-sulfophenyl)-5-[(phenylamino)carbonyl]-2H-tetrazolium hydroxide), (0.5 mg/mL stock).25 µL of the resulting mixture was added to each well, followed by 2 hours shaking at 37° C. Growth was assessed spectrophotometrically by measuring the appearance of soluble formazan stain at 450/650 nm using an $E_{max}$ micro plate reader. Validation of the assay was confirmed by determination of the A. fumigatus minimum inhibitory concentration (MIC) for amphotericin B. MICs were also scored visually.

EXAMPLE 5
In vivo efficacy against fluconazole-resistant and fluconazole-sensitive candidiasis in mice Immunocompetent mice (ICR, Sprague-Dawley, Indianapolis, IN) were infected with a pathogenic strain (# 64) of Candida albicans which is sensitive to fluconazole. After 24 hours, dissemination of infection was shown by organ colony counts (kidney, spleen, and liver) greater than $10^5$ CFU. Treatment began 24 hours after infection with the indicated dosage once a day for 10 days. One group received 20 mg/kg of the compound administered via oral gavage in 0.1 mL. The test compound was formulated in 40% polyethyleneglycol (MW 400). Another group received 40 mg/kg of th compound, administered as above. A third group received polyethylene glycol, and the last group received fluconazole dosed orally at 40 mg/kg twice a day.

After 30 days the percent survival in the group treated with fluconazole and the group treated with test compound (40 mg per kg body weight, twice a day) was measured. In addition, the organ fungal load was measured at days 1, 10, and 30.

The test group had a median survival rate of 17.5 days, compared to 7 days for the vehicle control (p=0.0018 log rank test). The effect of the test compound was dose-responsive. The effect of 40 mg/kg of the test compound was similar to that of 40 mg/kg administered twice daily (p=0.2892) in this model. Fungal burden in kidney, liver, and spleen on days 10 and 30 was also measured. After 10 days, the fungal organ burdens in the kidney, liver, and spleen of mice treated with either concentration of the test compound were found to be less than or equal to one half the burdens in the same organs of mice treated with fluconazole.

In an similar experiment using a fluconazole-resistant clinical isolate (C. albicans UTR-14), the percent survival after 20 days of the group treated with a test compound or fluconazole at a dosage of 40 mg/kg body weight p.o. is measured.

EXAMPLE 6
Inhibition of Candida and Aspergillus

Following the U.S. National Committee on Clinical Laboratory Standards (NCCLS) (Ref. NCCLS Document M27-P, Volume 12, No. 25, December 1992, ISSN# 0273-3099). Broad-spectrum activity of a compound of formula (I) where $R_{14}$ ismethyl and $R_{13}$ is hydroxyl was confirmed against C. albicans, fluconazole-resistant C. albicans, C. tropicalis, C. krusei, C. glabrata, A. flavus, and A. fumigatus. Minimum inhibitory concentrations (MICs) at 24 hours ranged between 16 and 64 µg/mL.

EXAMPLE 7
Diterpene Derivatives Formulae (ii)
Extraction and separation of SM-F and SM-G Dried powdered root bark (500 g) of Swarizia madagascariensis Desv. was extracted by $CH_2Cl_2$ at room temperature 3×3,000 ml (24 hours, 140 rpm shaking). The solvent was removed under reduced pressure (700 mbar, 30 C) and the $CH_2Cl_2$ extract (47.0 g) was fractionated by column chromatography on silica gel with petroleum ether/EtOAc 2:1 to afford fraction D (12.68 g). A part of this material (6.0 g) was fractionated by medium pressure liquid chromatography on a Diol support with petroleum ether/EtOAc 7:1 to provide fraction F (2.58 g). This fraction was purified by medium pressure liquid chromatography on a Diol support with petroleum ether/$CH_2Cl_2$ to provide SM-F and SM-G as a mixture (1.11 g). SM-F and SM-G are (R) hydroxy and (S) hydroxy epimers, respectively, of formula ii wherein $R_{13}$ is —O— bonded to $R_{14}$ and $R_{14}$ is —CHOH.

Extraction and separation of SM-C and SM-D

Dried powdered root bark (500 g) of Swartzia madagascariensis Desv. was extracted by $CH_2Cl_2$ at room temperature 3×3,000 ml (24 hours, 140 rpm shaking). The solvent was removed under reduced pressure (700 mbar, 30 C) and the CH$_2$Cl$_2$ extract (47.0 g) was fractionated by column chromatography on silica gel with petroleum ether/EtOAc 2:1 to afford fraction C (2.25 g). A part of this material (0.60 g) was purified by medium pressure liquid chromatography on a Diol support with petroleum ether/CH$_2$Cl$_2$/iPrOH 95:5:0.5 to provide SM-C (15 mg) and SM-D (15 mg). SM-C and SM-D are (R) ethoxy and (S) ethoxy epimers, respectively, of formula ii wherein R$_{13}$ is —O— bonded to R$_{14}$ and R$_{14}$ is —CHOEt.

Extraction and separation of SM-E1 and SM-E2

Dried powdered root bark (500 g) of *Swartzia madagascariensis* Desv. was extracted by CH$_2$Cl$_2$ at room temperature 3×3,000 ml (24 hours, 140 rpm shaking). The solvent was removed under reduced pressure (700 mbar, 30 C) and the CH2Cl$_2$ extract (47.0 g) was fractionated by column chromatography on silica gel with petroleum ether/EtOAc 2:1 to afford fraction B (0.92 g). A part of this material (0.20 g) was purified by medium pressure liquid chromatography on a Diol support with petroleum ether/CH$_2$Cl$_2$/iPrOH 95:5:0.2 to provide SM-E1 and SM-E2 as a mixture (22 mg). SM-E1 and SM-E2 are (R) and (S) epimers, respectively, of formula ii wherein R$_{13}$ is —O— bonded to R$_{14}$ and R$_{14}$ is —CHOR$_a$, where R$_a$ is formula (a).

EXAMPLE 8

Inhibition of Dermatophytes

The in vitro activity of formula (I) against the dermatophytes *Trichophyton rubrum*, *Trichophyton mentagrophytes*, and *Epidermophyton floccosum* was measured. The data were collected after incubating for 96 hours. The average MIC (range) and number of isolates for the three dermatophytes was, respectively, 5 μg/mL (2–8 μg/mL) and 10; 2.7 μg/mL (0.5–8 μg/mL) and 13; and 4 μg/mL (--), and 1.

EXAMPLE 9

Toxicity Study

Four doses (0, 100, 300, and 1000 mg/kg) were formulated in 0.5% carboxymethylcellulose was administered once to CD-1 mice via oral gavage. Each dose group included three male mice and three female mice. General clinical observations (including weight gain and mortality) were made for 8 days. At the end of the study, observations were made regarding gross anatomical pathology. All of the mice survived without unusual clinical observations, except for one female mouse in the 1000 mg/kg category. Weight loss, abnormal gait and stance, and piloerection were observed on days 3–6, followed by mortality on day 7.

Based on the above, acute oral administration up to 300 mg/kg was well-tolerated. As acute toxicity generally manifests shortly after dosing, it was unclear whether the mortality of the sin-le female mouse indicates toxicity.

Use

In addition to the disclosed compound, the invention provides pharmaceutical compositions comprising one or more disclosed compounds and a pharmaceutical carrier. The invention also provides methods which include administering the disclosed compounds alone, or as a composition, to treat or inhibit microbial infection. Accordingly, one aspect of the invention is a method for treating a microbial infection wherein the fungal infection is resistant to, or sensitive to, an azole antifungal agent, such as fluconazole. The methods of the invention may further include co-administration of a second antimicrobial agent, resulting in administration of an antifungal agent and an antibacterial agent.

Fungal infections include fungal infections (mycoses), which may be cutaneous, subcutaneous, or systemic. Superficial mycoses include tinea capitis, tinea corporis, tinea pedis, onychomycosis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections include opportunistic fungal infections, particularly in immunocompromised patients such as those with AIDS. Fungal infections contribute to meningitis and pulmonary or respiratory tract diseases.

Pathogenic organisms include dermatophytes (e.g., *Microsporum canis* and other M. spp.; and Trichophyton spp. such as *T. rubrum*, and *T. mentagrophytes*), yeasts (e.g., *Candida albicans, C. Tropicalis*, or other Candida species), *Torulopsis glabrata, Epidermophytonfloccosum, Malassezia fuurfur* (*Pityropsporon orbiculare*, or *P. ovale*), *Cryptococcus neoformans, Aspergillusfumigatus*, and other Aspergillus spp., Zygomycetes (e.g., Rhizopus, Mucor), *Paracoccidioides brasiliensis, Blastomyces dermatitides, Histoplasma capsulatum, Coccidioides immitis*, and *Sporothrix schenckii*. Fungal infections include *Cladosporium cucumerinum, Epidermophyton floccosum*, and *Microspermum ypseum*. Current antimycotic drugs include nystatin, clotrimazole, amphotericin B, ketoconazole, fluconazole, and itraconazole.

Bacterial infections result in diseases such as bacteremia, pneumonia, meningitis, osteomyelitis, endocarditis, sinusitis, arthritis, urinary tract infections, tetanus, gangrene, colitis, acute gastroenteritis, bronchitis, and a variety of abscesses, nosocomial infections, and opportunistic infections. Bacterial pathogens include Gram-positive cocci such as *Staphylococcus aureus, Streptococcus pyogenes* (group A), Streptococcus spp. (viridans group), *Streptococcus agalactiae* (group B), *S. bovis*, Streptococcus (anaerobic species), *Streptococcus pneumoniae*, and Enterococcus spp.; Gram-negative cocci such as *Neisseria gonorrhoeae, Neisseria meningitidis*, and *Branhamella catarrhalis*; Gram-positive bacilli such as *Bacillus anthracis, Corynebacterium diphtheriae* and Corynebacterium species which are diptheroids (aerobic and anaerobic), *Listeria monocytogenes, Clostridium tetani, Clostridium difficile, Escherichia coli*, Enterobacter species, *Proteus mirabilis* and other spp., *Pseudomonas aeruginosa, Klebsiella pneumoniae*, Salmonella, Shigella, Serratia, and *Campylobacterjejuni*. See Goodman and Gilman's Pharmacological Basis of Therapeutics, (8th ed., 1990) Table 44-1, page 1024–1033, for additional microbial pathogens, diseases, and current therapeutic agents.

Administration and Formulation

An antimicrobial composition of the invention can be formulated for administration by injection (e.g., intravenous, intraocular, intraperitoneal, and intramuscular), oral administration (e.g., tablets, capsules, powders, and drops), and topical administration (e.g., tinctures, creams, lotions, gels, sprays, drops, and impregnated bandages). Typical regimens include 0.05%–5% topical eyedrops or eye ointments, 0.01%–5% topical creams, and oral or intravenous formulations for about 5 to about 21 days. The antimicrobial composition can be administered therapeutically or prophylactically. A disclosed composition contains from about 0.01% to 90% by weight (such as about 0.1% to 20% or about 0.5% to 10%) of a disclosed compound.

The concentration of active ingredient in each pharmaceutical formulation and the effective amount of the active compound used to treat a given condition will vary, depending upon the mode of administration, the age and the body weight of the patient, and the condition to be treated. Such amount of the active compound as determined by the attending physician or veterinarian is referred to herein as "effective amount."

In addition to appropriate carriers or excipients, and optional absorption enhancers, the compositions of the invention can also contain one or more additional therapeutic agents, such as anti-inflammatory agents, anti-viral agents, or analgesics. Alternatively, the method of treatment may include separate administration of an additional pharmaceutical composition containing another antimicrobial agent, or other therapeutic agent. A composition of the invention may be formulated for various methods of administration, and may further be formulated for controlled release, such as an implant, transdermal patch, or a capsule.

Other Embodiments

From the above description, one skilled in the art can easily ascertain the essential characteristics of the present invention, and without departing from the spirit and scope thereof, can make various changes and modifications of the invention to adapt it to various usages and conditions.

Other embodiments of the invention provide a method of inhibiting a microbial infection which includes exposing an animal in need of such exposure to a pharmaceutically effective amount of a metabolite of a compound of formula (I), or a prodrug or metabolic precursor of a metabolite of a compound of formula (I).

What is claimed is:

1. A pharmaceutical composition comprising a compound having the formula (I):

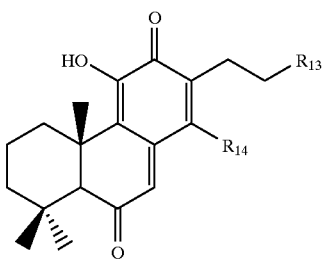

(I)

wherein $R_{14}$ is methyl and $R_{13}$ is hydroxyl; or $R_{13}$ is —O— bonded to $R_{14}$ and $R_{14}$ is —CHOR$_a$—, $R_a$ being hydrogen, $C_{1-4}$ alkyl, or formula (a) below:

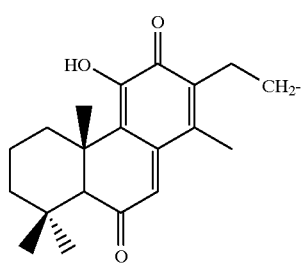

(a)

2. A pharmaceutical composition comprising a compound of claim 1, wherein $R_{13}$ is —O— bonded to $R_{14}$ and $R_{14}$ is —CHOR$_a$—, $R_a$ being hydrogen, $C_{1-4}$ alkyl, or formula (a).

3. A pharmaceutical composition comprising a compound of claim 1, wherein $R_{14}$ is methyl and $R_{13}$ is hydroxyl.

4. A method for inhibiting a fungal infection, said method comprising administering a pharmaceutical composition including a compound having the formula (I):

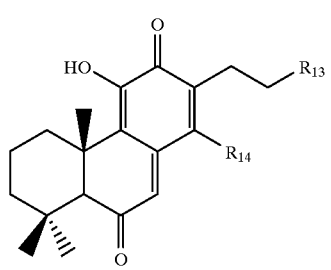

(I)

wherein $R_{14}$ is methyl and $R_{13}$ is hydroxyl; or $R_{13}$ is —O— bonded to $R_{14}$ and $R_{14}$ is —CHOR$_a$—, $R_a$ being hydrogen, $C_{1-4}$ alkyl, or formula (a) below:

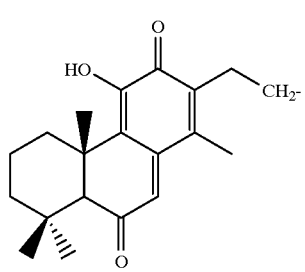

(a)

5. A method of claim 4, wherein said fungal infection is an infection of a Candida species.

6. A method of claim 5, wherein said Candkia species is *C. albicans*, *C. krusei*, or *C. glabrata*.

7. A method of claim 4, wherein said fungal infection is an infection of an Aspergillus species.

8. A method of claim 7, wherein said Aspergillus species is *A. fumigatus*, *A. niger*, or *A. flavus*.

9. A method of claim 4, wherein said fungal infection is resistant to, or sensitive to, an azole antifungal agent.

10. A method of claim 9, wherein said azole antifungal agent is fluconazole.

11. A method of claim 4, further comprising co-administration of a second antimicrobial agent.

12. A method for inhibiting a bacterial infection, said method comprising administering a pharmaceutical composition including a compound having the formula (I):

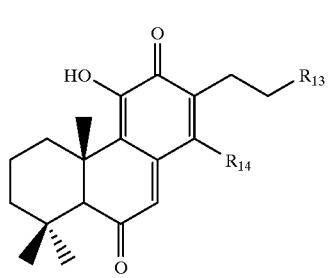

(I)

wherein $R_{14}$ is methyl and $R_{13}$ is hydroxyl; or $R_{13}$ is —O— bonded to $R_{14}$ and $R_{14}$ is —CHOR$_a$—, $R_a$ being hydrogen, $C_{1-4}$ alkyl, or formula (a) below:

(a)

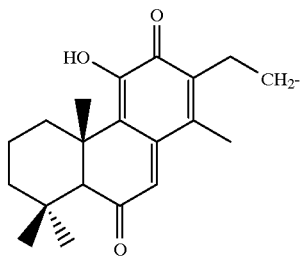

13. A method of claim 12, wherein said bacterial infection is an infection of a Staphylococcus species.

14. A method of claim 13, wherein said Staphylococcus species is *S. aureus* or *S. epidermidis*.

15. A method of claim 11, wherein said microbial infection is an infection of the skin, hair, or nails.

16. A method of claim 15, wherein said microbial infection is an infection of a dermatophyte selected from Trichophyton and Epidrnophyton spp.

17. A method of claim 16, wherein said dermatophyte is selected Frye *T. rubrum, T. mentagrophytes*, and *E. floccosum*.

18. A method of claim 15, wherein said microbial infection onychomycosis.

* * * * *

UNITED STATES PATENT AND TRADEMARK OFFICE
CERTIFICATE OF CORRECTION

PATENT NO.: 5,929,124
DATED: July 27, 1999
INVENTORS: Kurt Hostettmann and Frederic Shaller It is certified that error appears in the above-identified patent and that said Letters Patent is hereby corrected as shown below: In the Claims:

Claim 16, replace "Epidrnophyton" with --Epidermophyton--.

Claim 17, replace "Frye" with --from--.

Claim 18, the word --is-- should be inserted between "infection" and "onychomycosis."

Signed and Sealed this

Twenty-first Day of March, 2000

Attest:

Attesting Officer

Q. TODD DICKINSON

Commissioner of Patents and Trademarks